| United States Patent [19] | [11] | 4,247,467 |
|---|---|---|
| Murib | [45] | Jan. 27, 1981 |

[54] PREPARATION OF GAMMA-LACTONES

[75] Inventor: Jawad H. Murib, Cincinnati, Ohio

[73] Assignee: National Distillers and Chemical Corp., New York, N.Y.

[21] Appl. No.: 972,857

[22] Filed: Dec. 26, 1978

[51] Int. Cl.$^3$ .......................................... C07D 307/32
[52] U.S. Cl. .................................. 260/343.6; 252/456
[58] Field of Search ..................................... 260/343.6

[56] References Cited

U.S. PATENT DOCUMENTS

| 3,758,514 | 9/1973 | Heiba et al. | 260/343.6 |
| 3,813,416 | 5/1974 | Heiba et al. | 260/343.6 |
| 3,845,116 | 10/1974 | Finkheiner et al. | 260/343.6 X |
| 3,992,417 | 11/1976 | Dessau et al. | 260/343.6 |
| 4,014,910 | 3/1977 | De Klein | 260/343.6 X |
| 4,081,456 | 3/1978 | Heiba et al. | 260/343.6 X |

FOREIGN PATENT DOCUMENTS

| 746757 | 9/1970 | Belgium | 260/343.6 |
| 1219331 | 1/1971 | United Kingdom | 260/343.6 |
| 1271092 | 4/1972 | United Kingdom . | |
| 1354466 | 5/1974 | United Kingdom | 260/343.6 |

*Primary Examiner*—Ethel G. Love
*Attorney, Agent, or Firm*—Kenneth D. Tremain

[57] ABSTRACT

A process for preparing gamma-lactones which comprises contacting an alpha-olefin, oxygen and a carboxylic acid containing an alpha-hydrogen atom in the vapor phase at an elevated temperature and at a controlled pressure in the presence of a catalytically effective amount of a catalyst comprising an oxide of uranium. The catalyst preferably also contains at least one oxide selected from the group consisting of arsenic, antimony and bismuth oxides. A preferred process comprises contacting ethylene, oxygen and acetic acid at atmospheric pressure in the presence of a catalyst consisting essentially of oxides of uranium and antimony to produce gamma-butyrolactone.

7 Claims, No Drawings

PREPARATION OF GAMMA-LACTONES

BACKGROUND OF THE INVENTION

This invention relates to a process for preparing gamma-lactones by the catalyzed oxyacylation of alpha-olefins.

Lactones are important industrial chemical products which are useful in a variety of applications. Gamma-lactones, and in particular gamma-butyrolactones, are particularly important as intermediates in the production of diol compounds such as 1,4-butanediol.

There are various known methods to prepare lactones as shown in "Advanced Organic Chemistry" by Fieser and Fieser, Reinhold Book Corporation, 1968, on pages 572–575. Thus, for example, gamma-lactones may be prepared from gamma-hydroxy acids by dehydration or by isomerization of unsaturated acids by heat or by treatment with hydrobromic or sulfuric acid. U.S. Pat. No. 3,890,361 to Kanetaka et al. describes the production of gamma-butyrolactones by catalytic hydrogenation of dicarboxylic anhydrides using a special nickel catalyst.

The preparation of lactones from olefins is also known. In an article by Heiba et al. entitled "Oxidation By Metal Salts. X. One-Step Synthesis of Gamma-Lactones from Olefins", Journal of the American Chemical Society/96:26/Dec. 25, 1974, the reaction of an olefin and a carboxylic acid having an alpha-hydrogen atom in the presence of stoichiometric amounts of a higher valent metal salt or oxide of manganese, cerium, or vanadium oxidant is disclosed. The reaction is carried out in a refluxing system at a temperature of 120°–180° C. Similar reactions using the vanadium catalyst are shown in Chemical Abstracts, Volume 72, 1970, 66402a, Volume 82, 1975, 5760a and Volume 84, 1976, 150211t.

It is an object of this invention to provide an improved process for the preparation of gamma-lactones from olefins. Other objects and advantages will become apparent from the following description.

SUMMARY OF THE INVENTION

It has now been discovered that gamma-lactones may be prepared by contacting an alpha-olefin, oxygen and a carboxylic acid containing an alpha-hydrogen atom in the vapor phase at elevated temperatures and a controlled pressure in the presence of a catalyst consisting essentially of an oxide of uranium. The general reaction for preparing gamma-lactones by the process of this invention may be illustrated by the following equation

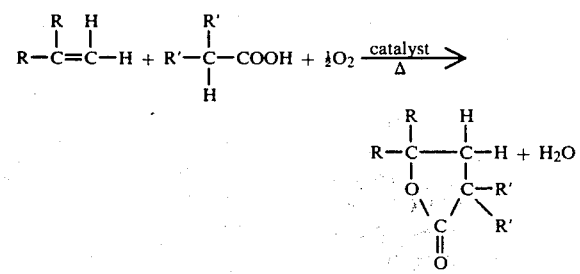

wherein R and R' are independently selected from the group consisting of hydrogen, alkyl, cycloalkyl, alkenyl, and aryl groups of 1–6 carbon atoms.

A preferred embodiment of the invention is to contact the alpha-olefin, oxygen and carboxylic acid in the vapor phase in the presence of a catalyst consisting essentially of an oxide of uranium and at least one oxide selected from the group consisting of arsenic, antimony and bismuth oxides. A fixed of fluidized catalyst bed may be suitably employed.

DETAILED DESCRIPTION OF THE INVENTION

The alpha-olefins useful in the process of the invention include mono- and diolefins containing from 2 to about 10 carbon atoms and may contain impurities of the type and in amounts normally present in the commercial grades of this reactant. The alpha-olefins may be substituted with aromatic or alicyclic groups and the diolefins may be conjugated or non-conjugated. Among the preferred alpha-olefins are those containing from 2 to about 8 carbon atoms, e.g., ethylene, propylene, butene-1, octene-1, butadiene, styrene and the like.

The carboxylic acids useful in the invention contain an alpha-hydrogen and from 2 to about 8 carbon atoms, preferably 2 to 6 carbon atoms. Lower carboxylic acids such as acetic and propionic acids are preferred. The carboxylic acids are suitable in their concentrated, commercial form. Aliphatic carboxylic acid having two or more COOH groups may also be employed.

In a highly preferred embodiment of the invention the alpha-olefin is ethylene and the carboxylic acid is acetic acid, with the valuable product being gamma-butyrolactone. Other exemplary products utilizing acetic acid are gamma-vinyl-gamma-butyrolactone from 1, 3-butadiene, gamma-caprolactone from butene-1 and gamma-valerolactone from propylene.

The oxygen may be pure oxygen gas or, alternatively, an oxygen-containing gas mixture such as air or air enriched with oxygen. In addition to these materials the oxygen may contain other inert dilutents such as carbon dioxide, nitrogen and the like.

The catalyst herein comprises an oxide of uranium and preferably, also contains at least one oxide selected from the group consisting of arsenic, antimony and bismuth. The aforestated oxides can exist in any of their oxidation states and be made from compounds of any oxidation states and specifically include uranium dioxide, uranyl uranate, uranium trioxide, the trioxides, tetroxides and pentoxides of arsenic, antimony and bismuth, and mixtures of these oxides. The atomic ratio of uranium to antimony, bismuth and/or arsenic can vary over wide limits and advantageously is within the ratio of about 50:1 to about 1:99. A ratio of 10:1 to 1:10 is preferred. U.S. Pat. No. 3,198,750 discloses a suitable catalyst containing mixed antimony oxide and uranium oxide and a method for preparing the catalyst, said patent being hereby incorporated by reference.

While it is not necessary to provide the catalysts of this invention with a support, it is generally advantageous to deposit the catalysts upon a carrier such as any of the known and conventional catalyst carrier materials since catalytic efficiency will thereby be significantly improved. Thus, the catalysts herein can advantageously be supported upon silica, alumina, zirconia, silica alumina, silicon carbide, alundum and inorganic silicate in an amount, by weight of metal of the supported catalyst, of about 1 percent to about 90 percent, preferably about 10 to 50 percent. A preferred catalyst contains about 5% to 30% antimony, bismuth or arsenic, preferably antimony, and 1% to 20% uranium, by weight of the supported catalyst. Silica is preferred as the support.

The catalyst may be prepared by known techniques, e.g., contacting a metal salt solution with the support, drying and calcining in an oxidizing atomsphere, e.g., in the presence of an air sweep. A range of drying temperature of 100°–120° C. and a calcining temperature of 350°–900° C. may be suitably employed. Non-supported catalysts may be prepared by precipitation of the soluble salt or salts from solution by, e.g., neutralization with aqueous ammonia solution, filtration, washing, drying and calcining.

A preferred method for preparing the catalyst comprises treating an extruded or pelletized support with an aqueous solution containing uranyl nitrate and/or antimony pentachloride and concentrated hydrochloric acid. The mixture is evaporated and the impregnated support is dried at 110°–120° C. followed by calcining in air at 450° C. for 12 hours, and 850° C. for an additional 12 hours. Examples of suitable water soluble metal compounds which can be used in the preparation of the supported catalysts include uranyl nitrate, uranyl chloride, uranyl sulfate, uranyl tetrachloride, arsenic acid, antimony pentachloride and bismuth nitrate. The catalyst bed can be a fixed bed employing a large particulate or pelleted catalyst or in the alternative, a fluidized bed of catalyst can be utilized.

The catalyst may also contain promoters, such as oxides of molybdenum, thallium, copper and silver which are useful, e.g., to improve the selectivity and reaction rate. Molybdenum is preferred because of its demonstrated effectiveness. The amount of promoter, by weight of metal on the supported catalyst, is generally within the range of about 0.1–10%, preferably about 0.5%–3.5%, e.g., 3%.

In general, any apparatus of the type suitable for carrying out reactions in the vapor phase can be used in carrying out the reaction of this invention. The reactor can be brought to the reaction temperature before or after the introduction of the reaction feed mixture. However, in a large-scale operation, it is preferred to carry out the process in a continuous manner and in such a system, the recirculation of unreacted reactants is contemplated.

The concentrations of olefin, carboxylic acid and oxygen used in the reaction can vary widely. The effective minimum concentration of catalyst will depend upon temperature, residence time and the particular composition of the catalyst employed. The mole ratios of oxygen to olefin to carboxylic acid fed to the reaction zone is not critical but it should be adjusted so that the mixture used is not in the explosive region. The stoichiometric ratio of alpha-olefin:carboxylic acid:oxygen is 2:2:1 and the relative proportions may vary widely. In general, the alpha-olefin may be used in large excess to improve the selectivity to the lactone. Broadly stated, in volume percent, based on the total content of alpha-olefin, carboxylic acid and oxygen, the oxygen is about 1%–50%, the carboxylic acid is about 1%–77% and the alpha-olefin is about 1%–98%. A preferred range is about 1% to 20% oxygen, 2% to 35% carboxylic acid and 45% to 97% alpha-olefin. The feed may also be diluted with nitrogen or other inert gas to maintain the mixture outside the explosive limits. Water may be advantageously employed in the reaction and may be present in amounts up to about 5 volume %. The water may be added by the use of aqueous solutions of the carboxylic acid, either fresh or from a recycle stream.

In general, the temperature in the reaction zone is sufficient to maintain the reactants in the vapor state and is about 200°–450° C., preferably about 250°–400° C., although higher or lower temperatures may be employed.

An important feature of the invention is the pressure in the reaction zone. In my copending applications filed concurrently herewith it is disclosed and claimed that the reaction processes are dependent mainly upon the olefin employed and the pressure in the reaction zone. Thus, for example, in this application, when alpha-olefins are reacted at low pressure, up to about 40 psig, gamma-lactones are formed, such as gamma-butyrolactone from ethylene. At high pressures, e.g., above about 40 psig, in the application entitled "Process for Preparing Ethylene Glycol Esters", oxyacylation of ethylene produces ethylene glycol esters and oxyacylation of higher olefins, e.g., propylene, in the application entitled "Process for Preparing Esters" produces allyl acetate as a major product. Similarly, oxyacylation of aromatics over a wide range of pressures described in the application entitled "Process for Preparing Aromatic Esters", produces esters, such as benzyl acetate from toluene. In the instant process, it is important to employ a pressure in the reaction zone of up to about 40 psig, preferably up to about 30 psig. A preferred range is about atmospheric to 20 psig.

The reaction time will depend largely upon the concentration of reactants and therefore, may suitably vary over a wide range. Flow rates are preferably adjusted so that the contact time is in the range of about 0.1 to about 60 seconds, and preferably between about 1 and 5 seconds. The product from the reaction may then be recovered by known methods, e.g., extraction, distillation, etc.

The following expressions are defined as follows and will be used throughout the disclosure.

The term "% Conversions" means $$\frac{\text{millimoles (MM) in} - \text{MM out}}{\text{MM in}} \times 100$$

of the specified reactant.

The term "% Selectivity Component" means $$\frac{\text{MM component}}{\text{MM specified material reacted}} \times 100$$

The term "Catalyst Utility" means grams component produced/liter catalyst/hour (g/l. cat/hr).

The following examples are illustrative of the invention.

EXAMPLE 1

Preparation of Catalyst

Extruded silica gel, 429.5 gram (g.) (⅛" diameter×¼" long, 200 m²/g surface area) was placed in a 2-liter beaker and treated with an aqueous solution containing 248.8 g. SbCl₅, 90.6 g. UO₂(NO₃)₂.6H₂O and 210 g. concentrated HCL. While mixing, the mixture was heated to dryness on a hot plate. The resulting impregnated extrudates were calcined in air at 450° C. for twelve hours followed by calcining in air at 850° C. for an additional twelve hours.

EXAMPLE 2

A 30 milliliter (ml.) stainless steel reactor 10 centimeter (cm.)×2 cm. (inside diameter) with a thermocouple was packed with 14.3 g. of the catalyst prepared above.

A gaseous stream of 296 cubic centimeters (cc.)/minute of, by volume, 88.9% ethylene, 7.4% acetic acid and 3.7% oxygen was passed through the reactor and contacted with the catalyst at one atmosphere pressure and about 350° C. The reactor effluent was bubbled through deionized water at 0° C. The non-condensible gases were measured by a wet-test meter and a sample of the gaseous mixture was analyzed for oxygen and carbon oxides (CO and $CO_2$). Analysis of the aqueous solution disclosed formation of gamma-butyrolactone at a Catalyst Utility of 2.8 g./l. cat/hr. as established by gas-liquid chromatography and mass spectroscopy. The % Selectivity to gamma-butyrolactone was 23.5% based on reacted acetic acid at 37% Conversion based on oxygen (the limiting reactant).

EXAMPLE 3

The procedure of Example 2 was repeated except the catalyst was supported on alumina pellets (⅛ inch×⅛ inch). A feed, by volume, of 89.6% ethylene, 8.4% acetic acid and 2% oxygen was passed through the reactor and contacted with the catalyst at 1 atmosphere, 337° C. and 1.5 seconds contact time. Analysis of the reactor effluent indicated formation of gamma-butyrolactone at a Catalyst Utility of 1.8 g./l. cat/hr. at 24.9% Selectivity based on reacted acetic acid and 49.2% Conversion based on oxygen.

EXAMPLE 4

Example 3 was repeated except that the catalyst contained mixed oxides of, by weight of catalyst, 27% antimony, 9% uranium and 3% molybdenum supported on silica and was heated at 362° C. Gamma-butyrolactone was obtained in 44.5% Conversion based on oxygen and at 26.4% Selectivity based on reacted acetic acid with a Catalyst Utility of 5.7 g. gamma-butyrolactone/l. cat./hr.

EXAMPLE 5

The procedure of Example 2 was repeated with a feed consisting of 6.1% propylene, 10.4% oxygen, 8.6% acetic acid, balance nitrogen. The feed was contacted at 1 atmosphere and with 8 g. of a non-supported catalyst containing mixed oxides of antimony and uranium (atomic ratio of U/Sb about 1:7). Gamma-valerolactone was obtained.

EXAMPLE 6

The procedure of Example 5 was repeated except that butene-1 was used instead of propylene. Gamma-caprolactone was produced.

EXAMPLE 7

The procedure of Example 5 was repeated except that butadiene was used instead of propylene. Gamma-vinyl-gamma-butyrolactone was obtained at a rate of about 13 g./l. cat./hr.

EXAMPLE 8

A feed of, by volume %, 88.9% ethylene, 7.4% acetic acid and 3.7% oxygen was contacted (contact time about 3 seconds) at a temperature of 340° C. with an alumina supported catalyst containing uranium oxide in an amount of about 6% by weight uranium. Gamma-butyrolactone was formed at a Catalyst Utility of 1.7 g/l. cat/hr. and a 5.3% Selectivity based on reacted acetic acid. Adding antimony oxide in an amount of about 2% by weight antimony to the catalyst increased the Catalyst Utility to 2.5 g/l. cat/hr. and % Selectivity to 9.9.

It will be apparent that many changes and modifications of the several features described herein may be made without departing from the spirit and scope of the invention. It is therefore apparent that the foregoing description is by way of illustration of the invention rather than limitation of the invention.

I claim:

1. A process for preparing gamma-lactones which comprises contacting oxygen, an alpha-olefin represented by the formula:

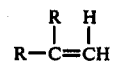

and a carboxylic acid containing an alpha-hydrogen atom represented by the formula:

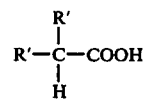

wherein R and R' are independently selected from the group consisting of hydrogen, alkyl, cycloalkyl, alkenyl and aryl groups of 1-6 carbon atoms; in the vapor phase at an elevated temperature and a pressure up to about 40 psig in the presence of a catalytically effective amount of a catalyst consisting essentially of an oxide of uranium and at least one oxide selected from the group consisting of arsenic, antimony and bismuth oxides.

2. A process as in claim 1 wherein the alpha-olefin contains from 2 to about 8 carbon atoms and the carboxylic acid contains from 2 to about 8 carbon atoms.

3. A process as in claim 1 wherein the catalyst is supported on a carrier.

4. A process as in claim 2 wherein the alpha-olefin is ethylene and the carboxylic acid is acetic acid and the catalyst is supported on a carrier.

5. A process as in claim 1 wherein in volume % based on the total content of alpha-olefin, carboxylic acid and oxygen, the oxygen is about 1%-50%, the carboxylic acid is about 1%-77% and the alpha-olefin is about 1%-98% and the temperature is about 200°-450° C.

6. A process for preparing gamma-lactones which comprises contacting oxygen, an alpha-olefin represented by the formula:

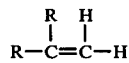

and a carboxylic acid containing an alpha-hydrogen atom represented by the formula:

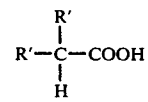

wherein R and R' are independently selected from the group consisting of hydrogen, alkyl, cycloalkyl, alkenyl and aryl groups of 1-6 carbon atoms; in the vapor phase at a temperature of about 200°-450° C. and a pressure up to about 40 psig in the presence of a catalytically effective amount of a supported catalyst consisting essentially of an oxide of uranium and at least one oxide selected from the group consisting of arsenic, antimony and bismuth oxides and wherein in volume % based on the total content of alpha-olefin, carboxylic acid and oxygen, the oxygen is about 1%–50%, the carboxylic acid is about 1%–77% and the alpha-olefin is about 1%–98% and wherein by weight of the supported catalyst, the catalyst contains about 5% to 30% antimony, bismuth or arsenic and about 1%–20% uranium.

7. A process as in claim 6 wherein the catalyst contains a molybdenum oxide promoter.

* * * * *